US008318966B2

(12) United States Patent
Meiere

(10) Patent No.: US 8,318,966 B2
(45) Date of Patent: Nov. 27, 2012

(54) ORGANOMETALLIC COMPOUNDS

(75) Inventor: Scott Houston Meiere, Williamsville, NY (US)

(73) Assignee: Praxair Technology, Inc., Danbury, CT (US)

( * ) Notice: Subject to any disclaimer, the term of this patent is extended or adjusted under 35 U.S.C. 154(b) by 1140 days.

(21) Appl. No.: 11/807,545

(22) Filed: May 29, 2007

(65) Prior Publication Data

US 2007/0299274 A1 Dec. 27, 2007

Related U.S. Application Data

(60) Provisional application No. 60/815,834, filed on Jun. 23, 2006.

(51) Int. Cl.
*C07F 7/02* (2006.01)
(52) U.S. Cl. ........................ 556/410; 556/407
(58) Field of Classification Search .................. 556/407, 556/410
See application file for complete search history.

(56) References Cited

U.S. PATENT DOCUMENTS

| | | | |
|---|---|---|---|
| 4,556,725 A | | 12/1985 | Kanner et al. |
| 4,654,309 A | * | 3/1987 | Mlinar et al. ................... 436/61 |
| 5,258,169 A | * | 11/1993 | Wannagat et al. ............ 423/344 |
| 5,976,991 A | | 11/1999 | Laxman et al. |
| 6,291,867 B1 | | 9/2001 | Wallace et al. |
| 6,365,231 B2 | | 4/2002 | Sato et al. |
| 6,399,208 B1 | | 6/2002 | Baum et al. |
| 6,869,638 B2 | | 3/2005 | Baum et al. |
| 6,963,006 B2 | | 11/2005 | Tsui et al. |
| 7,122,222 B2 | | 10/2006 | Xiao et al. |
| 2004/0043149 A1 | | 3/2004 | Gordon et al. |
| 2005/0023625 A1 | | 2/2005 | Ahn et al. |
| 2005/0048204 A1 | * | 3/2005 | Dussarrat et al. .......... 427/248.1 |
| 2006/0062917 A1 | | 3/2006 | Muthukrishnan et al. |
| 2006/0193984 A1 | * | 8/2006 | Peters et al. .................. 427/252 |

FOREIGN PATENT DOCUMENTS

JP 04-055398 2/1992

OTHER PUBLICATIONS

Schmidt et al., {p-Bond strengths in the second and third periods, Journal of the American Chemical Society (1987), 109(17), 5217-27}.*
Cheng et al., {Preparation of a microporous silicon oximide gel from the reaction of tris(dimethylamino)silylamine with formamide and its pyrolytic conversion into a silicon oxynitride based glass, Journal of Materials Chemistry (2005), 15(29),3039-3044}.*
Kaskel et al., {Synthesis, Characterization, and Catalytic Properties of High-Surface-Area Aluminum Silicon Nitride Based Materials, Chemistry of Materials (2005), 17(1), 181-185}.*
Cheng et al., {Preparation of mesoporous silicon nitride via a nonaqueous sol-gel route, Journal of the American Ceramic Society (2004), 87(8), 1413-1417}.*
Passarelli et al., {Aminolysis of the Si-Cl bond and ligand exchange reaction between silicon amido derivatives and SiCl4: synthetic applications and kinetic investigations, Dalton Transactions (2003), (3), 413-419}.*
Dhiman et al, Organometallics, 2004, 23, 5689-5693.*
JP 2005213633(English abstract only), 2005.*
SK284151(English abstract only), 2004.*
Katrin et al, Ber. Chem(English abstract only), 1997.*
Cai, et al., "The stable silylene $Si[(NCH_2Bu)_2C_6H_4-1,2]$: insertion into Li-C or Li-Si bonds of lithium alkyls LiR or $[LiSi(SiMe_3)_3(THF)_3]$ [R = Me, $^tBu$ or $CH(SiMe_3)_2$]", Journal of Organometallic Chemistry 643-644 (2002) pp. 272-277.
Heinicke, et al., "Unsymmetrical Carbene Homologues: Isolable Pyrido[$b$]-1,3,$22^2$-diazasilole, -germole and -stannole and Quantum-Chemical Comparison with Unstable Pyrido[$c$] Isomers", Chem. Eur. J. 1998, 4, No. 3, (1998) pp. 541-545.
Haaf, et al., "Synthesis and Reactivity of a Stable Silylene", J. Am. Chem. Soc. (1998), 120, pp. 12714-12719.
Gehrhus, et al., "Synthesis, structures and oxidative addition reactions of new thermally stable silylenes; crystal structures of $[Si\{N(CH_2{}^tBu)\}_2C_6H_4-1,2]$ and $[(Si \{N(CH_2{}^tBu)\}_2C6H4-1,2)(u-E)]_2$ (E—Se or Te)$^{1}$", Journal of Organometallic Chemistry 521 (1996) pp. 211-220.
Bradley, et al.,"Non-Oxide Sol-Gel Chemistry: . . . ", Agnew Chem. Int. Ed. 1999 38 13 2036.
Wolfe, et al., "Remote Plasma Enhanced-Metal Organic Chemical Vapor . . . " Mat Res. Soc. Symp. Proc. 1999 567 343.
Lucovsky, et al., "Microscopic model for enhanced dielectric constants in low concentration SiO2-rich nonccystalline Zr and Hf silicate alloys", Appl. Phys. Let. 2000 77 18 29.
Gordon, et al., "Vapor Deposition of Metal Oxides and Silicates: Possible Gate Insulators for Future Microelectronics" Chem. Mater. 2001 13 2463.
Hendrix, et al., "Composition control of Hf1-xSixO2 films deposited on Si by chemical-vapor deposition using amide precursors", Appl. Phys. Let. 2002 2002 80 13 2362.
Bradley, et al., "Syntheses and structures of [Me3N)3SiNHLi], (C4H8O)Al[NHSi(NMe2)3]3 . . . " Dalton Trans 2003 1846-1851.
Hoover, et al., "High-K Dielectric Precursors: Synthesis and Deposition", Semiconductor Manufacturing Jun. 2004.
Owang, et al., "Implementing a batch atomic layer deposition approach for advanced DRAM dielectrics", Micro 2005 23 2 49.

* cited by examiner

*Primary Examiner* — Shailendra Kumar
(74) *Attorney, Agent, or Firm* — Nilay S. Dalal

(57) ABSTRACT

This invention relates to organometallic compounds represented by the formula $H_aM(NR_1R_2)_x(NR_3H)_y(NH_2)_z$ wherein M is a metal or metalloid, each of $R_1$, $R_2$ and $R_3$ is the same or different and is independently a hydrocarbon group or a heteroatom-containing group, a is a value from 0 to 3, x is a value from 0 to 3, y is a value from 0 to 4, z is a value from 0 to 4, and a+x+y+z is equal to the oxidation state of M, provided that at least one of y and z is a value of at least 1, a process for producing the organometallic compounds, and a method for producing a film or coating from organometallic precursor compounds.

2 Claims, No Drawings

US 8,318,966 B2

ORGANOMETALLIC COMPOUNDS

RELATED APPLICATION

This application claims the benefit of U.S. Provisional Application Ser. No. 60/815,834, filed on Jun. 23, 2006.

FIELD OF THE INVENTION

This invention relates to organometallic compounds represented by the formula $H_aM(NR_1R_2)_x(NR_3H)_y(NH_2)_z$ wherein M is a metal or metalloid, each of $R_1$, $R_2$ and $R_3$ is the same or different and is independently a hydrocarbon group or a heteroatom-containing group, a is a value from 0 to 3, x is a value from 0 to 3, y is a value from 0 to 4, z is a value from 0 to 4, and a+x+y+z is equal to the oxidation state of M, provided that at least one of y and z is a value of at least 1, a process for producing the organometallic compounds, and a method for producing a film or coating from organometallic precursor compounds.

BACKGROUND OF THE INVENTION

Chemical vapor deposition methods are employed to form films of material on substrates such as wafers or other surfaces during the manufacture or processing of semiconductors. In chemical vapor deposition, a chemical vapor deposition precursor, also known as a chemical vapor deposition chemical compound, is decomposed thermally, chemically, photochemically or by plasma activation, to form a thin film having a desired composition. For instance, a vapor phase chemical vapor deposition precursor can be contacted with a substrate that is heated to a temperature higher than the decomposition temperature of the precursor, to form a metal or metal oxide film on the substrate. Preferably, chemical vapor deposition precursors are volatile, heat decomposable and capable of producing uniform films under chemical vapor deposition conditions.

The semiconductor industry is currently considering the use of thin films of various metals for a variety of applications. Many organometallic complexes have been evaluated as potential precursors for the formation of these thin films. A need exists in the industry for developing new compounds and for exploring their potential as chemical vapor deposition precursors for film depositions.

For the chemical vapor deposition of silicon-containing films (e.g., $SiO_2$), compounds such as silane, chlorinated silanes, and alkoxy silanes (e.g., TEOS) are well known. However, as next generation oxide materials with higher dielectric constants, so called 'high-k' materials (e.g., $HfO_2$), are integrated, and concurrently new precursors are developed for these materials (e.g., hafnium amides), other silicon precursors will require development for the deposition of ternary systems and beyond (e.g., hafnium silicates).

For silicon amide compounds with cyclic amide ligands, an example reported in the literature is tetrakis(pyrrolidinyl) silane (a solid at room temperature, mp=30° C.). Inorg. Nucl. Chem. Letters 1969 5 733 discloses tetrakis(pyrrolidinyl) silane compound and a low yield synthetic method for preparation thereof.

U.S. Patent Application Publication Nos. US 2002/0187644 A1 and US 2002/0175393 A1 disclose metalloamide precursor compositions having stated utility for forming dielectric thin films such as gate dielectric, high dielectric constant metal oxides, and ferroelectric metal oxides and to a low temperature chemical vapor deposition process for deposition of such dielectric thin films utilizing the compositions.

A need exists in the industry for an improved silicon dioxide atomic layer deposition precursors. Although many silicon precursors are readily available (e.g., silane, tetrachlorosilane, tetraethoxysilane, tetrakis(dimethylamino)silane), none of these silicon precursors have the desired optimal properties of an atomic layer deposition precursor for certain applications. One of these applications is for a nanolaminate structures in tandem with other materials, for example a high-k material such as $HfO_2$. For this application, a balance of reactivity and thermal stability must be achieved to grow self-limiting $SiO_2$ with an adequate growth rate. Compounds such as silane may be too unstable, tetrachlorosilane may yield halogen impurities, and tetraethoxysilane and tetrakis (dimethylamino)silane may be too unreactive within the temperature parameters of the application. The problem is therefore to generate a suitable atomic layer deposition precursor for such an application.

Further, in developing methods for forming thin films by chemical vapor deposition or atomic layer deposition methods, a need continues to exist for precursors that preferably are liquid at room temperature, have adequate vapor pressure, have appropriate thermal stability (i.e., for chemical vapor deposition will decompose on the heated substrate but not during delivery, and for atomic layer deposition will not decompose thermally but will react when exposed to co-reactant), can form uniform films, and will leave behind very little, if any, undesired impurities (e.g., halides, carbon, etc.). Therefore, a need continues to exist for developing new compounds and for exploring their potential as chemical vapor or atomic layer deposition precursors for film depositions. It would therefore be desirable in the art to provide a precursor that possesses some, or preferably all, of the above characteristics.

SUMMARY OF THE INVENTION

This invention relates in part to organometallic compounds represented by the formula $H_aM(NR_1R_2)_x(NR_3H)_y(NH_2)_z$ wherein M is a metal or metalloid, $R_1$ is the same or different and is a hydrocarbon group or a heteroatom-containing group, $R_2$ is the same or different and is a hydrocarbon group or a heteroatom-containing group, $R_3$ is the same or different and is a hydrocarbon group or a heteroatom-containing group, a is a value from 0 to 3, x is a value from 0 to 3, y is a value from 0 to 4, z is a value from 0 to 4, and a+x+y+z is equal to the oxidation state of M, provided that at least one of y and z is a value of at least 1.

More particularly, this invention relates in part to organometallic compounds represented by the formula $H_aSi(NR_1R_2)_x(NR_3H)_y(NH_2)_z$ wherein $R_1$ is the same or different and is a hydrocarbon group or a heteroatom-containing group, $R_2$ is the same or different and is a hydrocarbon group or a heteroatom-containing group, $R_3$ is the same or different and is a hydrocarbon group or a heteroatom-containing group, a is a value from 0 to 3, x is a value from 0 to 3, y is a value from 0 to 4, z is a value from 0 to 4, and a+x+y+z=4, provided that at least one of y and z is a value of at least 1.

This invention also relates in part to organometallic compounds represented by the formula :$M(NR'_1R'_2)_q$ wherein M is a metal or metalloid, $R'_1$ is the same or different and is a hydrocarbon group or a heteroatom-containing group, $R'_2$ is the same or different and is a hydrocarbon group or a heteroatom-containing group; when q is a value of 2 or greater, $R'_1$ or $R'_2$ of one $(NR'_1R'_2)$ group can be combined with $R'_1$ or $R'_2$ of another $(NR'_1R'_2)$ group to form a substituted or unsubstituted, saturated or unsaturated cyclic group; q is a value equal to or less than the oxidation state of M, and : represents 2 electrons.

More particularly, this invention also relates in part to organometallic compounds represented by the formula :Si(NR'$_1$R'$_2$)$_2$ wherein R'$_1$ is the same or different and is a hydrocarbon group or a heteroatom-containing group, R'$_2$ is the same or different and is a hydrocarbon group or a heteroatom-containing group; R'$_1$ or R'$_2$ of one (NR'$_1$R'$_2$) group can be combined with R'$_1$ or R'$_2$ of another (NR'$_1$R'$_2$) group to form a substituted or unsubstituted, saturated or unsaturated cyclic group; and : represents 2 electrons.

This invention further relates in part to a process for the production of an organometallic compound comprising (i) reacting in a first pot a nitrogen-containing compound with an alkali metal, or an alkali metal-containing compound, or an alkaline earth metal, or an alkaline earth metal-containing compound, in the presence of a solvent and under reaction conditions sufficient to produce a first reaction mixture comprising a base material, (ii) adding said base material to a second pot containing a metal source compound and optionally an amine compound, (iii) reacting in said second pot said base material with said metal source compound and optionally said amine compound under reaction conditions sufficient to produce a second reaction mixture comprising said organometallic compound, and (iv) separating said organometallic compound from said second reaction mixture; wherein said organometallic compound is represented by the formula H$_a$M(NR$_1$R$_2$)$_x$(NR$_3$H)$_y$(NH$_2$)$_z$ in which M is a metal or metalloid, R$_1$ is the same or different and is a hydrocarbon group or a heteroatom-containing group, R$_2$ is the same or different and is a hydrocarbon group or a heteroatom-containing group, R$_3$ is the same or different and is a hydrocarbon group or a heteroatom-containing group, a is a value from 0 to 3, x is a value from 0 to 3, y is a value from 0 to 4, z is a value from 0 to 4, and a+x+y+z is equal to the oxidation state of M, provided that at least one of y and z is a value of at least 1. The organometallic compound yield resulting from the process of this invention can be 60% or greater, preferably 75% or greater, and more preferably 90% or greater.

More particularly, this invention further relates in part to a process for the production of an organometallic compound comprising (i) reacting in a first pot a nitrogen-containing compound with an alkali metal, or an alkali metal-containing compound, or an alkaline earth metal, or an alkaline earth metal-containing compound, in the presence of a solvent and under reaction conditions sufficient to produce a first reaction mixture comprising a base material, (ii) adding said base material to a second pot containing a metal source compound and optionally an amine compound, (iii) reacting in said second pot said base material with said metal source compound and optionally said amine compound under reaction conditions sufficient to produce a second reaction mixture comprising said organometallic compound, and (iv) separating said organometallic compound from said second reaction mixture; wherein said organometallic compound is represented by the formula H$_a$Si(NR$_1$R$_2$)$_x$(NR$_3$H)$_y$(NH$_2$)$_z$ wherein R$_1$ is the same or different and is a hydrocarbon group or a heteroatom-containing group, R$_2$ is the same or different and is a hydrocarbon group or a heteroatom-containing group, R$_3$ is the same or different and is a hydrocarbon group or a heteroatom-containing group, a is a value from 0 to 3, x is a value from 0 to 3, y is a value from 0 to 4, z is a value from 0 to 4, and a+x+y+z=4, provided that at least one of y and z is a value of at least 1. The organometallic compound yield resulting from the process of this invention can be 60% or greater, preferably 75% or greater, and more preferably 90% or greater.

This invention yet further relates in part to a process for the production of an organometallic compound comprising (i) reacting in a first pot a nitrogen-containing compound with an alkali metal, or an alkali metal-containing compound, or an alkaline earth metal, or an alkaline earth metal-containing compound, in the presence of a solvent and under reaction conditions sufficient to produce a first reaction mixture comprising a base material, (ii) adding said base material to a second pot containing a metal source compound and optionally an amine compound, (iii) reacting in said second pot said base material with said metal source compound and optionally said amine compound under reaction conditions sufficient to produce a second reaction mixture comprising an organometallic compound derivative, (iv) subjecting said second reaction mixture to reduction or dehalogenation under conditions sufficient produce a third reaction mixture comprising said organometallic compound, and (v) separating said organometallic compound from said third reaction mixture; wherein said organometallic compound is represented by the formula :M(NR'$_1$R'$_2$)$_q$ wherein M is a metal or metalloid, R'$_1$ is the same or different and is a hydrocarbon group or a heteroatom-containing group, R'$_2$ is the same or different and is a hydrocarbon group or a heteroatom-containing group; when q is a value of 2 or greater, R'$_1$ or R'$_2$ of one (NR'$_1$R'$_2$) group can be combined with R'$_1$ or R'$_2$ of another (NR'$_1$R'$_2$) group to form a substituted or unsubstituted, saturated or unsaturated cyclic group; q is a value equal to or less than the oxidation state of M, and : represents 2 electrons. The organometallic compound yield resulting from the process of this invention can be 60% or greater, preferably 75% or greater, and more preferably 90% or greater.

More particularly, this invention yet further relates in part to a process for the production of an organometallic compound comprising (i) reacting in a first pot a nitrogen-containing compound with an alkali metal, or an alkali metal-containing compound, or an alkaline earth metal, or an alkaline earth metal-containing compound, in the presence of a solvent and under reaction conditions sufficient to produce a first reaction mixture comprising a base material, (ii) adding said base material to a second pot containing a metal source compound and optionally an amine compound, (iii) reacting in said second pot said base material with said metal source compound and optionally said amine compound under reaction conditions sufficient to produce a second reaction mixture comprising an organometallic compound derivative, (iv) subjecting said second reaction mixture to reduction or dehalogenation under conditions sufficient produce a third reaction mixture comprising said organometallic compound, and (v) separating said organometallic compound from said third reaction mixture; wherein said organometallic compound is represented by the formula :Si(NR'$_1$R'$_2$)$_2$ wherein R'$_1$ is the same or different and is a hydrocarbon group or a heteroatom-containing group, R'$_2$ is the same or different and is a hydrocarbon group or a heteroatom-containing group; R'$_1$ or R'$_2$ of one (NR'$_1$R'$_2$) group can be combined with R'$_1$ or R'$_2$ of another (NR'$_1$R'$_2$) group to form a substituted or unsubstituted, saturated or unsaturated cyclic group; and : represents 2 electrons. The organometallic compound yield resulting from the process of this invention can be 60% or greater, preferably 75% or greater, and more preferably 90% or greater.

This invention also relates in part to a method for producing a film, coating or powder by decomposing an organometallic precursor compound represented by the formula H$_a$M $(NR_1R_2)_x(NR_3H)_y(NH_2)_z$ wherein M is a metal or metalloid, $R_1$ is the same or different and is a hydrocarbon group or a heteroatom-containing group, $R_2$ is the same or different and is a hydrocarbon group or a heteroatom-containing group, $R_3$ is the same or different and is a hydrocarbon group or a heteroatom-containing group, a is a value from 0 to 3, x is a value from 0 to 3, y is a value from 0 to 4, z is a value from 0 to 4, and a+x+y+z is equal to the oxidation state of M, provided that at least one of y and z is a value of at least 1, thereby producing the film, coating or powder. Typically, the decomposing of said organometallic precursor compound is thermal, chemical, photochemical or plasma-activated.

More particularly, this invention also relates in part to a method for producing a film, coating or powder by decomposing an organometallic precursor compound represented by the formula $H_aSi(NR_1R_2)_x(NR_3H)_y(NH_2)_z$ wherein $R_1$ is the same or different and is a hydrocarbon group or a heteroatom-containing group, $R_2$ is the same or different and is a hydrocarbon group or a heteroatom-containing group, $R_3$ is the same or different and is a hydrocarbon group or a heteroatom-containing group, a is a value from 0 to 3, x is a value from 0 to 3, y is a value from 0 to 4, z is a value from 0 to 4, and a+x+y+z=4, provided that at least one of y and z is a value of at least 1, thereby producing the film, coating or powder. Typically, the decomposing of said organometallic precursor compound is thermal, chemical, photochemical or plasma-activated.

This invention further relates in part to a method for producing a film, coating or powder by decomposing an organometallic precursor compound represented by the formula :$M(NR'_1R'_2)_q$ wherein M is a metal or metalloid, $R'_1$ is the same or different and is a hydrocarbon group or a heteroatom-containing group, $R'_2$ is the same or different and is a hydrocarbon group or a heteroatom-containing group; when q is a value of 2 or greater, $R'_1$ or $R'_2$ of one $(NR'_1R'_2)$ group can be combined with $R'_1$ or $R'_2$ of another $(NR'_1R'_2)$ group to form a substituted or unsubstituted, saturated or unsaturated cyclic group; q is a value equal to or less than the oxidation state of M, and : represents 2 electrons, thereby producing the film, coating or powder. Typically, the decomposing of said organometallic precursor compound is thermal, chemical, photochemical or plasma-activated.

More particularly, this invention further relates in part to a method for producing a film, coating or powder by decomposing an organometallic precursor compound represented by the formula :$Si(NR'_1R'_2)_2$ wherein $R'_1$ is the same or different and is a hydrocarbon group or a heteroatom-containing group, $R'_2$ is the same or different and is a hydrocarbon group or a heteroatom-containing group; $R'_1$ or $R'_2$ of one $(NR'_1R'_2)$ group can be combined with $R'_1$ or $R'_2$ of another $(NR_{11}R'_2)$ group to form a substituted or unsubstituted, saturated or unsaturated cyclic group; and : represents 2 electrons, thereby producing the film, coating or powder. Typically, the decomposing of said organometallic precursor compound is thermal, chemical, photochemical or plasma-activated.

This invention yet further relates in part to organometallic precursor compound mixtures comprising (i) a first organometallic precursor compound represented by the formula $H_aM(NR_1R_2)_x(NR_3H)_y(NH_2)_z$ wherein M is a metal or metalloid, $R_1$ is the same or different and is a hydrocarbon group or a heteroatom-containing group, $R_2$ is the same or different and is a hydrocarbon group or a heteroatom-containing group, $R_3$ is the same or different and is a hydrocarbon group or a heteroatom-containing group, a is a value from 0 to 3, x is a value from 0 to 3, y is a value from 0 to 4, z is a value from 0 to 4, and a+x+y+z is equal to the oxidation state of M, provided that at least one of y and z is a value of at least 1, and (ii) one or more different organometallic precursor compounds (e.g., a hafnium-containing, tantalum-containing or molybdenum-containing organometallic precursor compound).

More particularly, this invention yet further relates in part to organometallic precursor compound mixtures comprising (i) a first organometallic precursor compound represented by the formula $H_aSi(NR_1R_2)_x(NR_3H)_y(NH_2)_z$ wherein $R_1$ is the same or different and is a hydrocarbon group or a heteroatom-containing group, $R_2$ is the same or different and is a hydrocarbon group or a heteroatom-containing group, $R_3$ is the same or different and is a hydrocarbon group or a heteroatom-containing group, a is a value from 0 to 3, x is a value from 0 to 3, y is a value from 0 to 4, z is a value from 0 to 4, and a+x+y+z=4, provided that at least one of y and z is a value of at least 1, and (ii) one or more different organometallic precursor compounds (e.g., a hafnium-containing, tantalum-containing or molybdenum-containing organometallic precursor compound).

This invention also relates in part to organometallic precursor compound mixtures comprising (i) a first organometallic precursor compound represented by the formula :$M(NR'_1R'_2)_q$ wherein M is a metal or metalloid, $R'_1$ is the same or different and is a hydrocarbon group or a heteroatom-containing group, $R'_2$ is the same or different and is a hydrocarbon group or a heteroatom-containing group; when q is a value of 2 or greater, $R'_1$ or $R'_2$ of one $(NR'_1R'_2)$ group can be combined with $R_{11}$ or $R'_2$ of another $(NR'_1R'_2)$ group to form a substituted or unsubstituted, saturated or unsaturated cyclic group; q is a value equal to or less than the oxidation state of M, and : represents 2 electrons, and (ii) one or more different organometallic precursor compounds (e.g., a hafnium-containing, tantalum-containing or molybdenum-containing organometallic precursor compound).

More particularly, this invention also relates in part to organometallic precursor compound mixtures comprising (i) a first organometallic precursor compound represented by the formula :$Si(NR'_1R'_2)_2$ wherein $R'_1$ is the same or different and is a hydrocarbon group or a heteroatom-containing group, $R'_2$ is the same or different and is a hydrocarbon group or a heteroatom-containing group; $R'_1$ or $R'_2$ of one $(NR'_1R'_2)$ group can be combined with $R'_1$ or $R'_2$ of another $(NR'_1R'_2)$ group to form a substituted or unsubstituted, saturated or unsaturated cyclic group; and : represents 2 electrons, and (ii) one or more different organometallic precursor compounds (e.g., a hafnium-containing, tantalum-containing or molybdenum-containing organometallic precursor compound).

This invention relates in particular to 'next generation' depositions involving amide-based silicon precursors. These precursors can have advantages over the other known precursors, especially when utilized in tandem with other 'next-generation' materials (e.g., hafnium, tantalum and molybdenum), for the formation of silicates, silicon oxynitrides, and the like. These silicon-containing materials can be used for a variety of purposes such as dielectrics, barriers, and electrodes, and in many cases show improved properties (thermal stability, desired morphology, less diffusion, lower leakage, less charge trapping, and the like) than the non-silicon containing films.

The invention has several advantages. For example, the processes of the invention are useful in generating organometallic compounds that have varied chemical structures and physical properties. Films generated from the organometallic compound precursors can be deposited with a short incubation time, and the films deposited from the organometallic compound precursors exhibit good smoothness.

This invention relates in particular to chemical vapor deposition and atomic layer deposition precursors for next generation devices, specifically organometallic precursors that are liquid at room temperature, i.e., 20° C.

The organometallic precursor compounds of this invention can provide desired properties of an atomic layer deposition precursor for applications involving nanolaminate structures in tandem with other materials, for example, a high-k material such as $HfO_2$. For this application, a balance of reactivity and thermal stability must be achieved to grow self-limiting $SiO_2$ with an adequate growth rate. Compounds such as silane may be too unstable, tetrachlorosilane may yield halogen impurities, and tetraethoxysilane and tetrakis(dimethylamino)silane may be too unreactive within the temperature parameters of the application. The organometallic precursor compounds of this invention can be suitable atomic layer deposition precursors for such an application.

DETAILED DESCRIPTION OF THE INVENTION

This invention involves the synthesis and use of silicon amide compounds that are comprised of at least one $-NH_2$ or $-NR_3H$ moiety (where $R_3$ is a hydrocarbon group or a heteroatom-containing group such as an alkyl (e.g., methyl, t-butyl)). The introduction of this type of ligand can increase the reactivity and/or decrease the thermal stability of the silicon precursor due to the presence of the N—H bond, which can allow for alternate reaction and/or decomposition pathways. This precursor can yield improved performance for $SiO_2$ deposition or other silicon based films (e.g., silicon nitride, hafnium silicate, etc.). The organometallic precursor compounds of this invention can yield a desired mix of thermal stability, reactivity and volatility for the desired application. Other structures may also be useful, for example, a hydroxyl ligand in tandem with amide ligands.

As indicated above, this invention relates to organometallic compounds represented by the formula $H_aM(NR_1R_2)_x(NR_3H)_y(NH_2)_z$ wherein M is a metal or metalloid, each of $R_1$, $R_2$ and $R_3$ is the same or different and is independently a hydrocarbon group or a heteroatom-containing group, a is a value from 0 to 3, preferably 0 or 1, x is a value from 0 to 3, preferably 2 or 3, y is a value from 0 to 4, preferably 0 or 1, z is a value from 0 to 4, preferably 1 or 2, and a+x+y+z is equal to the oxidation state of M, provided that at least one of y and z is a value of at least 1. For purposes of this invention, with respect to organometallic compounds (but not precursors) of the above formula, when M is Si, a is a value of 0, x is a value of 3, y is a value of 0, z is a value of 1, then one of $R_1$ and $R_2$ is other than methyl. Also, for purposes of this invention, with respect to organometallic compounds and precursors of the above formula, when M is Si, a is a value of 2, x is a value of 0, y is a value of 2, z is a value of 0, then $R_3$ is other than tert-butyl.

Typically, $R_1$, $R_2$ and $R_3$ are the same or different and are independently hydrogen, alkyl; a substituted or unsubstituted, saturated or unsaturated, hydrocarbon, aromatic hydrocarbon, cycloaliphatic hydrocarbon, aromatic heterocycle, cycloaliphatic heterocycle, alkyl halide, silylated hydrocarbon, ether, polyether, thioether, ester, lactone, amide, amine, polyamine, nitrile; or mixtures thereof. $R_1$, $R_2$ and $R_3$ can also include substituted or unsubstituted, saturated or unsaturated, cyclic amido or amino groups, for example, aziridinyl, azetidinyl, pyrrolidinyl, thiazolidinyl, piperidinyl, pyrrolyl, pyridinyl, pyrimidinyl, pyrrolinyl, pyrazolyl, thiazolyl, oxazolyl, imidazolyl, imidazolidinonyl, imidazolidinethionyl, quinolinyl, isoquinolinyl, carbazolyl, triazolyl, indolyl and purinyl. Preferably, each of $R_1$, $R_2$ and $R_3$ is the same or different and is independently hydrogen, alkyl, or mixtures thereof. Typically, M is selected from Si, Ti, Zr, Hf, V, Nb, Ta, Cr, Mo, W, Al, Ga, Ge, a Lanthanide series element or an Actinide series element.

As also indicated above, this invention relates in part to organometallic compounds represented by the formula $:M(N'_1R'_2)_q$ wherein M is a metal or metalloid, $R'_1$ is the same or different and is a hydrocarbon group or a heteroatom-containing group, $R'_2$ is the same or different and is a hydrocarbon group or a heteroatom-containing group; when q is a value of 2 or greater, $R'_1$ or $R'_2$ of one $(NR'_1R'_2)$ group can be combined with $R'_1$ or $R'_2$ of another $(NR'_1R'_2)$ group to form a substituted or unsubstituted, saturated or unsaturated cyclic group; q is a value equal to or less than the oxidation state of M, and : represents 2 electrons. Typically, the oxidation state of M is a value of q or q+2. For purposes of this invention, with respect to organometallic compounds (but not precursors) of the above formula, when M is Si, $R_1$ is tert-butyl, $R_2$ is CH, x is a value of 2, then the $R_2$ groups cannot be bound together by a carbon-carbon double bond creating a cyclic system.

Typically, $R'_1$ and $R'_2$ are the same or different and are independently hydrogen, alkyl; a substituted or unsubstituted, saturated or unsaturated, hydrocarbon, aromatic hydrocarbon, cycloaliphatic hydrocarbon, aromatic heterocycle, cycloaliphatic heterocycle, alkyl halide, silylated hydrocarbon, ether, polyether, thioether, ester, lactone, amide, amine, polyamine, nitrile; or mixtures thereof. $R'_1$ and $R'_2$ can also include substituted or unsubstituted, saturated or unsaturated, cyclic amido or amino groups, for example, aziridinyl, azetidinyl, pyrrolidinyl, thiazolidinyl, piperidinyl, pyrrolyl, pyridinyl, pyrimidinyl, pyrrolinyl, pyrazolyl, thiazolyl, oxazolyl, imidazolyl, imidazolidinonyl, imidazolidinethionyl, quinolinyl, isoquinolinyl, carbazolyl, triazolyl, indolyl and purinyl. Preferably, each of $R'_1$ and $R'_2$ is the same or different and is independently hydrogen, alkyl, or mixtures thereof, or $R'_1$ or $R_{12}$ of one $(NR'_1R'_2)$ group can be combined with $R'_1$ or $R'_2$ of another $(NR'_1R'_2)$ group to form a substituted or unsubstituted, saturated or unsaturated cyclic group.

In a preferred embodiment, this invention relates to organometallic compounds represented by the formula $H_aSi(NR_1R_2)_x(NR_3H)_y(NH_2)_z$ wherein each of $R_1$, $R_2$ and $R_3$ is the same or different and is independently a hydrocarbon group or a heteroatom-containing group, a is a value from 0 to 3, preferably 0 or 1, x is a value from 0 to 3, preferably 2 or 3, y is a value from 0 to 4, preferably 0 or 1, z is a value from 0 to 4, preferably 1 or 2, and a+x+y+z=4, provided that at least one of y and z is a value of at least 1. For purposes of this invention, with respect to organometallic compounds (but not precursors) of the above formula, when a is a value of 0, x is a value of 3, y is a value of 0, z is a value of 1, then one of $R_1$ and $R_2$ is other than methyl. Also, for purposes of this invention, with respect to organometallic compounds and precursors of the above formula, when a is a value of 2, x is a value of 0, y is a value of 2, z is a value of 0, then $R_3$ is other than tert-butyl.

In another preferred embodiment, this invention relates to organometallic compounds represented by the formula $:Si(NR'_1R'_2)_2$ wherein $R'_1$ is the same or different and is a hydrocarbon group or a heteroatom-containing group, $R'_2$ is the same or different and is a hydrocarbon group or a heteroatom-containing group; $R'_1$ or $R'_2$ of one $(NR'_1R'_2)$ group can be combined with $R'_1$ or $R'_2$ of another $(NR'_1R'_2)$ group to form a substituted or unsubstituted, saturated or unsaturated cyclic group; and : represents 2 electrons. For purposes of this invention, with respect to organometallic compounds (but not precursors) of the above formula, when $R_1$ is tert-butyl, $R_2$ is CH, x is a value of 2, then the $R_2$ groups cannot be bound together by a carbon-carbon double bond creating a cyclic system.

Illustrative organometallic compounds of this invention include, for example, tris(dimethylamino)silylamine, tris(pyrrolyl)silylamine, tris(2-methylpyrrolidinyl)silylamine, tris(imidazolyl)silylamine, tris(1-methylpiperazinyl)silylamine, tris(pyrazolyl)silylamine, tetrakis(ethylamino)silane, tris(dimethylamino)(ethylamino)silane, N,N'-di-tert-butylethene-1,2-diaminosilylene, N,N'-di-tert-butylethylene-1,2-diaminosilylene, N,N'-diisopropylethene-1,2-diaminosilylene, bis(di-tert-butylamino)silylene, bis(di-tert-amylamino)silylene, and the like.

Illustrative organometallic compounds of this invention can be represented by the formulae:

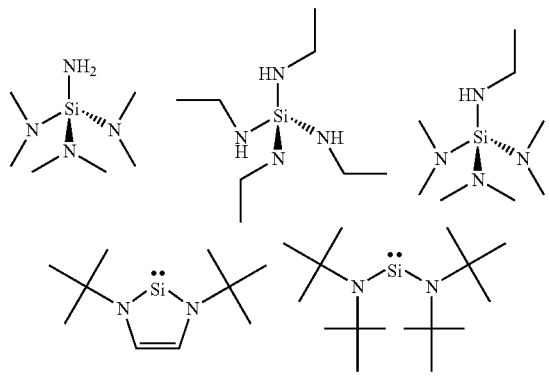

The organometallic precursor compounds of this invention may be homoleptic, i.e., all R radicals are the same such as tetrakis(ethylamino)silane or heteroleptic, i.e., one or more of the R radicals are different from each other such as tris(ethylmethylamino)(tert-butylamino)silane.

As indicated above, this invention also relates to a process for the production of an organometallic compound comprising (i) reacting in a first pot a nitrogen-containing compound with an alkali metal, or an alkali metal-containing compound, or an alkaline earth metal, or an alkaline earth metal-containing compound, in the presence of a solvent and under reaction conditions sufficient to produce a first reaction mixture comprising a base material, (ii) adding said base material to a second pot containing a metal source compound and optionally an amine compound, (iii) reacting in said second pot said base material with said metal source compound and optionally said amine compound under reaction conditions sufficient to produce a second reaction mixture comprising said organometallic compound, and (iv) separating said organometallic compound from said second reaction mixture; wherein said organometallic compound is represented by the formula $H_aM(NR_1R_2)_x(NR_3H)_y(NH_2)_z$ in which M is a metal or metalloid, each of $R_1$, $R_2$ and $R_3$ is the same or different and is independently a hydrocarbon group or a heteroatom-containing group, a is a value from 0 to 3, preferably 0 or 1, x is a value from 0 to 3, preferably 2 or 3, y is a value from 0 to 4, preferably 0 or 1, z is a value from 0 to 4, preferably 1 or 2, and a+x+y+z is equal to the oxidation state of M, provided that at least one of y and z is a value of at least 1. The organometallic compound yield resulting from the process of this invention can be 60% or greater, preferably 75% or greater, and more preferably 90% or greater.

As also indicated above, this invention relates in part to a process for the production of an organometallic compound comprising (i) reacting in a first pot a nitrogen-containing compound with an alkali metal, or an alkali metal-containing compound, or an alkaline earth metal, or an alkaline earth metal-containing compound, in the presence of a solvent and under reaction conditions sufficient to produce a first reaction mixture comprising a base material, (ii) adding said base material to a second pot containing a metal source compound and optionally an amine compound, (iii) reacting in said second pot said base material with said metal source compound and optionally said amine compound under reaction conditions sufficient to produce a second reaction mixture comprising an organometallic compound derivative, (iv) subjecting said second reaction mixture to reduction or dehalogenation under conditions sufficient produce a third reaction mixture comprising said organometallic compound, and (v) separating said organometallic compound from said third reaction mixture; wherein said organometallic compound is represented by the formula $:M(NR'_1R'_2)_q$ wherein M is a metal or metalloid, $R'_1$ is the same or different and is a hydrocarbon group or a heteroatom-containing group, $R'_2$ is the same or different and is a hydrocarbon group or a heteroatom-containing group; when q is a value of 2 or greater, $R'_1$ or $R'_2$ of one $(NR'_1R'_2)$ group can be combined with $R'_1$ or $R'_2$ of another $(NR'_1R'_2)$ group to form a substituted or unsubstituted, saturated or unsaturated cyclic group; q is a value equal to or less than the oxidation state of M, and : represents 2 electrons. The organometallic compound yield resulting from the process of this invention can be 60% or greater, preferably 75% or greater, and more preferably 90% or greater.

In a preferred embodiment, this invention relates to a process for the production of an organometallic compound comprising (i) reacting in a first pot a nitrogen-containing compound with an alkali metal, or an alkali metal-containing compound, or an alkaline earth metal, or an alkaline earth metal-containing compound, in the presence of a solvent and under reaction conditions sufficient to produce a first reaction mixture comprising a base material, (ii) adding said base material to a second pot containing a metal source compound and optionally an amine compound, (iii) reacting in said second pot said base material with said metal source compound and optionally said amine compound under reaction conditions sufficient to produce a second reaction mixture comprising said organometallic compound, and (iv) separating said organometallic compound from said second reaction mixture; wherein said organometallic compound is represented by the formula $H_aSi(NR_1R_2)_x(NR_3H)_y(NH_2)_z$ wherein each of each of $R_1$, $R_2$ and $R_3$ is the same or different and is independently a hydrocarbon group or a heteroatom-containing group, a is a value from 0 to 3, preferably 0 or 1, x is a value from 0 to 3, preferably 2 or 3, y is a value from 0 to 4, preferably 0 or 1, z is a value from 0 to 4, preferably 1 or 2, and a+x+y+z=4, provided that at least one of y and z is a value of at least 1. The organometallic compound yield resulting from the process of this invention can be 60% or greater, preferably 75% or greater, and more preferably 90% or greater.

In another preferred embodiment, this invention relates in part to a process for the production of an organometallic compound comprising (i) reacting in a first pot a nitrogen-containing compound with an alkali metal, or an alkali metal-containing compound, or an alkaline earth metal, or an alkaline earth metal-containing compound, in the presence of a solvent and under reaction conditions sufficient to produce a first reaction mixture comprising a base material, (ii) adding said base material to a second pot containing a metal source compound and optionally an amine compound, (iii) reacting in said second pot said base material with said metal source compound and optionally said amine compound under reaction conditions sufficient to produce a second reaction mixture comprising an organometallic compound derivative, (iv) subjecting said second reaction mixture to reduction or dehalogenation under conditions sufficient produce a third reaction mixture comprising said organometallic compound, and (v) separating said organometallic compound from said third reaction mixture; wherein said organometallic compound is represented by the formula :Si(NR'$_1$R'$_2$)$_2$ wherein R'$_1$ is the same or different and is a hydrocarbon group or a heteroatom-containing group, R'$_2$ is the same or different and is a hydrocarbon group or a heteroatom-containing group; R'$_1$ or R'$_2$ of one (NR'$_1$R'$_2$) group can be combined with R'$_1$ or R'$_2$ of another (NR'$_1$R'$_2$) group to form a substituted or unsubstituted, saturated or unsaturated cyclic group; and : represents 2 electrons. The organometallic compound yield resulting from the process of this invention can be 60% or greater, preferably 75% or greater, and more preferably 90% or greater.

In the processes described herein, the metal source compound, e.g., $SiCl_4$, $HSiCl_3$, $H_2SiCl_2$, tris(dimethylamino)chlorosilane, and the like, starting material may be selected from a wide variety of compounds known in the art. The invention herein most prefers metals selected from Si, Ti, Zr, Hf, V, Nb, Ta, Cr, Mo, W, Al, Ga, Ge, a Lanthanide series element or an Actinide series element. Illustrative metal source compounds include, for example, $SiCl_4$, $HSiCl_3$, $H_2SiCl_2$, $HSiCl_3$, tris(dimethylamino)chlorosilane, and the like. Other illustrative metal source compounds include, for example, $SiH_4$, $SiBr_4$, $HSiBr_3$, $SiI_4$, $HSiI_3$, and the like. The metal source compound starting material can typically be any compound or pure metal containing the central metal atom.

In an embodiment, the metal source compound can be represented by the formula $(H)_mM(X)_n$ wherein M is Si, Ti, Zr, Hf, V, Nb, Ta, Cr, Mo, W, Al, Ga, Ge, a Lanthanide series element or an Actinide series element, X is halide, m is from 0 to a value less than the oxidation state of M, n is from 1 to a value equal to the oxidation state of M, and m+n is a value equal to the oxidation state of M. Preferred metal source compounds include, for example, tetrachlorosilane, tetrabromosilane, hafnium tetrachloride, bis(dimethylamino)dichlorosilane, bis(diethylamino)dichlorosilane, bis(diethylamino)silane, (N,N'-di-tert-butylethene-1,2-diamino)dichlorosilane, (N,N'-di-tert-butylethylene-1,2-diamino)dichlorosilane, (N,N'-diisopropylethene-1,2-diamino)dichlorosilane, bis(di-tert-butylamino)dichlorosilane, or bis(di-tert-amylamino)dichlorosilane.

The concentration of the metal source compound starting material can vary over a wide range, and need only be that minimum amount necessary to react with the base material and optionally the amine compound and to provide the given metal concentration desired to be employed and which will furnish the basis for at least the amount of metal necessary for the organometallic compounds of this invention. In general, depending on the size of the reaction mixture, metal source compound starting material concentrations in the range of from about 1 millimole or less to about 10,000 millimoles or greater, should be sufficient for most processes.

In the processes described herein, the amine compounds may be selected from a wide variety of compounds known in the art. Illustrative amine compounds include, for example, dimethylamine, di-t-amylamine, ammonia, tert-butylamine, and the like. Preferred amine compound starting materials can be represented by the formula $NR_4R_5R_6$ wherein each of $R_4$, $R_5$ and $R_6$ is the same or different and is independently hydrogen, alkyl; a substituted or unsubstituted, saturated or unsaturated, hydrocarbon, aromatic hydrocarbon, cycloaliphatic hydrocarbon, aromatic heterocycle, alkyl halide, silylated hydrocarbon, ether, polyether, thioether, ester, lactone, amide, amine, polyamine, nitrile; or mixtures thereof. The amine compounds can include cyclic and chelating systems. The amine compounds can also include the HCl salt of amines such as ammonium chloride, dimethylammonium chloride, and the like. Preferably, each of $R_4$, $R_5$ and $R_6$ is the same or different and is independently hydrogen, alkyl, or mixtures thereof. Preferred amine compounds include, for example, ammonia, ethylamine, t-butylamine, di-tert-butylamine, di-tert-amylamine, N,N'-di-tert-butylethylene-1,2-diamine, N,N'-diisopropylethene-1,2-diamine, or N,N'-di-tert-butylethene-1,2-diamine.

The concentration of the amine compound starting material can vary over a wide range, and need only be that minimum amount necessary to react with the base starting material and metal source compound. In general, depending on the size of the reaction mixture, amine compound starting material concentrations in the range of from about 1 millimole or less to about 10,000 millimoles or greater, should be sufficient for most processes.

In the processes described herein, the base starting material may be selected from a wide variety of compounds known in the art. Illustrative bases include any base with a pKa greater than about 10, preferably greater than about 20, and more preferably greater than about 25. The base material is preferably $LiNH_2$, $LiNMe_2$, lithium amides and the like. Preferred base starting materials include, for example, lithium amide, lithium ethylamide, sodium ethylamide, lithium t-butylamide, lithium di-tert-butylamide, lithium di-tert-amylamide, lithium N,N'-di-tert-butylethylene-1,2-diamide, lithium N,N'-diisopropylethene-1,2-diamide, or lithium N,N'-di-tert-butylethene-1,2-diamide.

The concentration of the base starting material can vary over a wide range, and need only be that minimum amount necessary to react with the amine compound starting material and metal source compound. In general, depending on the size of the first reaction mixture, base starting material concentrations in the range of from about 1 millimole or less to about 10,000 millimoles or greater, should be sufficient for most processes.

In one embodiment, the base starting material may be generated in situ, for example, lithiated amides, lithiated amines, lithiated diamides, lithiated diamines, and the like. Generating the base starting material in situ in the reaction vessel immediately prior to reaction with the metal source compound is beneficial from a purity standpoint by eliminating the need to isolate and handle any reactive solids. It is also less expensive.

With the in situ generated base starting material in place, addition of the metal source compound, e.g., $SiCl_4$, can be performed through liquid or solid addition, or in some cases more conveniently as a solvent solution or slurry. Although certain metal source compounds are moisture sensitive and are used under an inert atmosphere such as nitrogen, it is generally to a much lower degree than the amine compounds, for example, lithiated amides, amines and the like. Furthermore, many metal source compounds are denser and easier to transfer.

The base starting material can be prepared from the reaction of a nitrogen-containing compound and an alkali metal, or an alkali metal-containing compound, or an alkaline earth metal, or an alkaline earth metal-containing compound. The base starting material can be prepared by conventional processes known in the art.

The solvent employed in the processes of this invention may be any saturated and unsaturated hydrocarbons, aromatic hydrocarbons, aromatic heterocycles, alkyl halides, silylated hydrocarbons, ethers, polyethers, thioethers, esters, thioesters, lactones, amides, amines, polyamines, nitrites, silicone oils, other aprotic solvents, or mixtures of one or more of the above; more preferably, pentanes, heptanes, octanes, nonanes, decanes, xylene, tetramethyl benzene, dimethoxyethanes, diglyme, fluorinated hydrocarbons, and mixtures of one or more of the above; and most preferably hexanes, ethers, THF, benzene, toluene, and mixtures of one of more of the above. Any suitable solvent which does not unduly adversely interfere with the intended reaction can be employed. Mixtures of one or more different solvents may be employed if desired. The amount of solvent employed is not critical to the subject invention and need only be that amount sufficient to solubilize the reaction components in the reaction mixture. In general, the amount of solvent may range from about 5 percent by weight up to about 99 percent by weight or more based on the total weight of the reaction mixture starting materials.

Reaction conditions for the processes for the reaction of the base material, the metal source compound, and optionally the amine compound, such as temperature, pressure and contact time, may also vary greatly and any suitable combination of such conditions may be employed herein. The reaction temperature may be the reflux temperature of any of the aforementioned solvents, and more preferably between about −80° C. to about 150° C., and most preferably between about 20° C. to about 80° C. Normally the reaction is carried out under ambient pressure and the contact time may vary from a matter of seconds or minutes to a few hours or greater. The reactants can be added to the reaction mixture or combined in any order. The stir time employed can range from about 0.1 to about 400 hours, preferably from about 1 to 75 hours, and more preferably from about 4 to 16 hours, for all steps. In the embodiment of this invention which is carried out in a single pot, the base material is not separated from the first reaction mixture prior to reacting with the metal source compound and optionally the amine compound. In a preferred embodiment, the metal source compound is added to the first reaction mixture at ambient temperature or at a temperature greater than ambient temperature.

Reaction conditions for the reduction or dehalogenation step, such as temperature, pressure and contact time, may also vary greatly and any suitable combination of such conditions may be employed herein. The reaction temperature may be the reflux temperature of any of the aforementioned solvents, and more preferably between about −80° C. to about 150° C., and most preferably between about 20° C. to about 80° C. Normally the reaction is carried out under ambient pressure and the contact time may vary from a matter of seconds or minutes to a few hours or greater. The reactants can be added to the reaction mixture or combined in any order. The stir time employed can range from about 0.1 to about 400 hours, preferably from about 1 to 75 hours, and more preferably from about 4 to 16 hours, for all steps. In the embodiment of this invention which is carried out in a single pot, the base material is not separated from the first reaction mixture prior to reacting with the metal source compound and optionally the amine compound. In a preferred embodiment, the metal source compound is added to the first reaction mixture at ambient temperature or at a temperature greater than ambient temperature. Typically, this step can be carried out using a variety of reagents, preferably an alkali metal (e.g., Na or K) is utilized.

The organometallic compounds prepared from the reaction of the base material, the metal source compound and optionally the amine compound may be selected from a wide variety of compounds. For purposes of this invention, organometallic compounds include compounds having a metal-nitrogen bond. Illustrative organometallic compounds include, for example, metal amides, metal amines and the like.

The organometallic compounds of this invention can also be prepared by a one pot process. The one pot process is particularly well-suited for large scale production since it can be conducted using the same equipment, some of the same reagents and process parameters that can easily be adapted to manufacture a wide range of products. The process provides for the synthesis of organometallic compounds using a process where all manipulations can be carried out in a single vessel, and which route to the organometallic compounds does not require the isolation of an intermediate complex. A one pot process is described in U.S. patent application Ser. No. 10/678,074, filed Oct. 6, 2003, which is incorporated herein by reference.

For organometallic compounds prepared by the processes of this invention, purification can occur through recrystallization, more preferably through extraction of reaction residue (e.g., hexane) and chromatography, and most preferably through sublimation and distillation.

Those skilled in the art will recognize that numerous changes may be made to the processes described in detail herein, without departing in scope or spirit from the present invention as more particularly defined in the claims below.

Examples of techniques that can be employed to characterize the organometallic compounds formed by the synthetic methods described above include, but are not limited to, analytical gas chromatography, nuclear magnetic resonance, thermogravimetric analysis, inductively coupled plasma mass spectrometry, differential scanning calorimetry, vapor pressure and viscosity measurements.

Relative vapor pressures, or relative volatility, of organometallic compound precursors described above can be measured by thermogravimetric analysis techniques known in the art. Equilibrium vapor pressures also can be measured, for example by evacuating all gases from a sealed vessel, after which vapors of the compounds are introduced to the vessel and the pressure is measured as known in the art.

The organometallic compound precursors described herein are preferably liquid at room temperature, i.e., 20° C., and are well suited for preparing in-situ powders and coatings. For instance, a liquid organometallic compound precursor can be applied to a substrate and then heated to a temperature sufficient to decompose the precursor, thereby forming a metal or metal oxide coating on the substrate. Applying a liquid precursor to the substrate can be by painting, spraying, dipping or by other techniques known in the art. Heating can be conducted in an oven, with a heat gun, by electrically heating the substrate, or by other means, as known in the art. A layered coating can be obtained by applying an organometallic compound precursor, and heating and decomposing it, thereby forming a first layer, followed by at least one other coating with the same or different precursors, and heating.

Liquid organometallic compound precursors such as described above also can be atomized and sprayed onto a substrate. Atomization and spraying means, such as nozzles, nebulizers and others, that can be employed are known in the art.

In preferred embodiments of the invention, an organometallic compound, such as described above, is employed in gas phase deposition techniques for forming powders, films or coatings. The compound can be employed as a single source precursor or can be used together with one or more other precursors, for instance, with vapor generated by heating at least one other organometallic compound or metal complex. More than one organometallic compound precursor, such as described above, also can be employed in a given process.

As indicated above, this invention relates to organometallic precursor mixtures comprising (i) a first organometallic precursor compound represented by the formula $H_aM(NR_1R_2)_x(NR_3H)_y(NH_2)_z$ wherein M is a metal or metalloid, each of $R_1$, $R_2$ and $R_3$ is the same or different and is independently a hydrocarbon group or a heteroatom-containing group, a is a value from 0 to 3, preferably 0 or 1, x is a value from 0 to 3, preferably 2 or 3, y is a value from 0 to 4, preferably 0 or 1, z is a value from 0 to 4, preferably 1 or 2, and a+x+y+z is equal to the oxidation state of M, provided that at least one of y and z is a value of at least 1, and (ii) one or more different organometallic precursor compounds. (e.g., a hafnium-containing, tantalum-containing or molybdenum-containing organometallic precursor compound).

As also indicated above, this invention relates to organometallic precursor compound mixtures comprising (i) a first organometallic precursor compound represented by the formula :$M(NR'_1R'_2)_q$ wherein M is a metal or metalloid, $R'_1$ is the same or different and is a hydrocarbon group or a heteroatom-containing group, $R'_2$ is the same or different and is a hydrocarbon group or a heteroatom-containing group; when q is a value of 2 or greater, $R'_1$ or $R'_2$ of one $(NR'_1R'_2)$ group can be combined with $R'_1$ or $R'_2$ of another $(NR'_1R'_2)$ group to form a substituted or unsubstituted, saturated or unsaturated cyclic group; q is a value equal to or less than the oxidation state of M, and : represents 2 electrons, and (ii) one or more different organometallic precursor compounds (e.g., a hafnium-containing, tantalum-containing or molybdenum-containing organometallic precursor compound).

In a preferred embodiment, this invention relates to organometallic precursor mixture comprising (i) a first organometallic precursor compound represented by the formula $H_aSi(NR_1R_2)_x(NR_3H)_y(NH_2)_z$ wherein each of $R_1$, $R_2$ and $R_3$ is the same or different and is independently a hydrocarbon group or a heteroatom-containing group, a is a value from 0 to 3, preferably 0 or 1, x is a value from 0 to 3, preferably 2 or 3, y is a value from 0 to 4, preferably 0 or 1, z is a value from 0 to 4, preferably 1 or 2, and a+x+y+z=4, provided that at least one of y and z is a value of at least 1, and (ii) one or more different organometallic precursor compounds (e.g., a hafnium-containing, tantalum-containing or molybdenum-containing organometallic precursor compound).

In another preferred embodiment, this invention relates to organometallic precursor compound mixtures comprising (i) a first organometallic precursor compound represented by the formula :$Si(NR'_1R'_2)_2$ wherein $R'_1$ is the same or different and is a hydrocarbon group or a heteroatom-containing group, $R'_2$ is the same or different and is a hydrocarbon group or a heteroatom-containing group; $R'_1$ or $R'_2$ of one $(NR'_1R'_2)$ group can be combined with $R'_1$ or $R'_2$ of another $(NR'_1R'_2)$ group to form a substituted or unsubstituted, saturated or unsaturated cyclic group; and : represents 2 electrons, and (ii) one or more different organometallic precursor compounds (e.g., a hafnium-containing, tantalum-containing or molybdenum-containing organometallic precursor compound).

Deposition can be conducted in the presence of other gas phase components. In an embodiment of the invention, film deposition is conducted in the presence of at least one non-reactive carrier gas. Examples of non-reactive gases include inert gases, e.g., nitrogen, argon, helium, as well as other gases that do not react with the organometallic compound precursor under process conditions. In other embodiments, film deposition is conducted in the presence of at least one reactive gas. Some of the reactive gases that can be employed include but are not limited to hydrazine, oxygen, hydrogen, air, oxygen-enriched air, ozone ($O_3$), nitrous oxide ($N_2O$), water vapor, organic vapors, ammonia and others. As known in the art, the presence of an oxidizing gas, such as, for example, air, oxygen, oxygen-enriched air, $O_3$, $N_2O$ or a vapor of an oxidizing organic compound, favors the formation of a metal oxide film.

As indicated above, this invention also relates in part to a method for producing a film, coating or powder. The method includes the step of decomposing at least one organometallic compound precursor, thereby producing the film, coating or powder, as further described below. More particularly, this invention relates in part to a method for producing a film, coating or powder by decomposing an organometallic precursor compound represented by the formula $H_aM(NR_1R_2)_x(NR_3H)_y(NH_2)_z$ wherein M is a metal or metalloid, each of $R_1$, $R_2$ and $R_3$ is the same or different and is independently a hydrocarbon group or a heteroatom-containing group, a is a value from 0 to 3, preferably 0 or 1, x is a value from 0 to 3, preferably 2 or 3, y is a value from 0 to 4, preferably 0 or 1, z is a value from 0 to 4, preferably 1 or 2, and a+x+y+z is equal to the oxidation state of M, provided that at least one of y and z is a value of at least 1, thereby producing the film, coating or powder. Typically, the decomposing of said organometallic precursor compound is thermal, chemical, photochemical or plasma-activated.

As also indicated above, this invention relates in part to a method for producing a film, coating or powder by decomposing an organometallic precursor compound represented by the formula :$M(NR'_1R'_2)_q$ wherein M is a metal or metalloid, $R'_1$ is the same or different and is a hydrocarbon group or a heteroatom-containing group, $R'_2$ is the same or different and is a hydrocarbon group or a heteroatom-containing group; when q is a value of 2 or greater, $R'_1$ or $R'_2$ of one $(NR'_1R'_2)$ group can be combined with $R'_1$ or $R'_2$ of another $(NR'_1R'_2)$ group to form a substituted or unsubstituted, saturated or unsaturated cyclic group; q is a value equal to or less than the oxidation state of M, and : represents 2 electrons, thereby producing the film, coating or powder. Typically, the decomposing of said organometallic precursor compound is thermal, chemical, photochemical or plasma-activated.

In a preferred embodiment, this invention relates to a method for producing a film, coating or powder by decomposing an organometallic precursor compound represented by the formula $H_aSi(NR_1R_2)_x(NR_3H)_y(NH_2)_z$ wherein each of $R_1$, $R_2$ and $R_3$ is the same or different and is independently a hydrocarbon group or a heteroatom-containing group, a is a value from 0 to 3, preferably 0 or 1, x is a value from 0 to 3, preferably 2 or 3, y is a value from 0 to 4, preferably 0 or 1, z is a value from 0 to 4, preferably 1 or 2, and a+x+y+z=4, provided that at least one of y and z is a value of at least 1, thereby producing the film, coating or powder. Typically, the decomposing of said organometallic precursor compound is thermal, chemical, photochemical or plasma-activated.

In another preferred embodiment, this invention relates in part to a method for producing a film, coating or powder by decomposing an organometallic precursor compound represented by the formula :$Si(NR'_1R'_2)_2$ wherein $R'_1$ is the same or different and is a hydrocarbon group or a heteroatom-containing group, $R'_2$ is the same or different and is a hydrocarbon group or a heteroatom-containing group; $R'_1$ or $R'_2$ of one $(NR'_1R'_2)$ group can be combined with $R'_1$ or $R'_2$ of another $(NR'_1R'_2)$ group to form a substituted or unsubstituted, saturated or unsaturated cyclic group; and : represents 2 electrons, thereby producing the film, coating or powder. Typically, the decomposing of said organometallic precursor compound is thermal, chemical, photochemical or plasma-activated.

Deposition methods described herein can be conducted to form a film, powder or coating that includes a single metal or a film, powder or coating that includes a single metal oxide.

Mixed films, powders or coatings also can be deposited, for instance mixed metal oxide films. A mixed metal oxide film can be formed, for example, by employing several organometallic precursors, at least one of which being selected from the organometallic compounds described above.

Gas phase film deposition can be conducted to form film layers of a desired thickness, for example, in the range of from about 1 nm to over 1 mm. The precursors described herein are particularly useful for producing thin films, e.g., films having a thickness in the range of from about 10 nm to about 100 nm. Films of this invention, for instance, can be considered for fabricating metal electrodes, in particular as n-channel metal electrodes in logic, as capacitor electrodes for DRAM applications, and as dielectric materials.

The method also is suited for preparing layered films, wherein at least two of the layers differ in phase or composition. Examples of layered film include metal-insulator-semiconductor, and metal-insulator-metal.

In an embodiment, the invention is directed to a method that includes the step of decomposing vapor of an organometallic compound precursor described above, thermally, chemically, photochemically or by plasma activation, thereby forming a film on a substrate. For instance, vapor generated by the compound is contacted with a substrate having a temperature sufficient to cause the organometallic compound to decompose and form a film on the substrate.

The organometallic compound precursors can be employed in chemical vapor deposition or, more specifically, in metalorganic chemical vapor deposition processes known in the art. For instance, the organometallic compound precursors described above can be used in atmospheric, as well as in low pressure, chemical vapor deposition processes. The compounds can be employed in hot wall chemical vapor deposition, a method in which the entire reaction chamber is heated, as well as in cold or warm wall type chemical vapor deposition, a technique in which only the substrate is being heated.

The organometallic compound precursors described above also can be used in plasma or photo-assisted chemical vapor deposition processes, in which the energy from a plasma or electromagnetic energy, respectively, is used to activate the chemical vapor deposition precursor. The compounds also can be employed in ion-beam, electron-beam assisted chemical vapor deposition processes in which, respectively, an ion beam or electron beam is directed to the substrate to supply energy for decomposing a chemical vapor deposition precursor. Laser-assisted chemical vapor deposition processes, in which laser light is directed to the substrate to affect photolytic reactions of the chemical vapor deposition precursor, also can be used.

The method of the invention can be conducted in various chemical vapor deposition reactors, such as, for instance, hot or cold-wall reactors, plasma-assisted, beam-assisted or laser-assisted reactors, as known in the art.

Examples of substrates that can be coated employing the method of the invention include solid substrates such as metal substrates, e.g., Al, Ni, Ti, Co, Pt, Ta; metal silicides, e.g., $TiSi_2$, $CoSi_2$, $NiSi_2$; semiconductor materials, e.g., Si, SiGe, GaAs, InP, diamond, GaN, SiC; insulators, e.g., $SiO_2$, $Si_3N_4$, $HfO_2$, $Ta_2O_5$, $Al_2O_3$, barium strontium titanate (BST); barrier materials, e.g., TiN, TaN; or on substrates that include combinations of materials. In addition, films or coatings can be formed on glass, ceramics, plastics, thermoset polymeric materials, and on other coatings or film layers. In preferred embodiments, film deposition is on a substrate used in the manufacture or processing of electronic components. In other embodiments, a substrate is employed to support a low resistivity conductor deposit that is stable in the presence of an oxidizer at high temperature or an optically transmitting film.

The method of this invention can be conducted to deposit a film on a substrate that has a smooth, flat surface. In an embodiment, the method is conducted to deposit a film on a substrate used in wafer manufacturing or processing. For instance, the method can be conducted to deposit a film on patterned substrates that include features such as trenches, holes or vias. Furthermore, the method of the invention also can be integrated with other steps in wafer manufacturing or processing, e.g., masking, etching and others.

Chemical vapor deposition films can be deposited to a desired thickness. For example, films formed can be less than 1 micron thick, preferably less than 500 nanometer and more preferably less than 200 nanometers thick. Films that are less than 50 nanometer thick, for instance, films that have a thickness between about 1 and about 20 nanometers, also can be produced.

Organometallic compound precursors described above also can be employed in the method of the invention to form films by atomic layer deposition (ALD) or atomic layer nucleation (ALN) techniques, during which a substrate is exposed to alternate pulses of precursor, oxidizer and inert gas streams. Sequential layer deposition techniques are described, for example, in U.S. Pat. No. 6,287,965 and in U.S. Pat. No. 6,342,277. The disclosures of both patents are incorporated herein by reference in their entirety.

For example, in one ALD cycle, a substrate is exposed, in step-wise manner, to: a) an inert gas; b) inert gas carrying precursor vapor; c) inert gas; and d) oxidizer, alone or together with inert gas. In general, each step can be as short as the equipment will permit (e.g. milliseconds) and as long as the process requires (e.g. several seconds or minutes). The duration of one cycle can be as short as milliseconds and as long as minutes. The cycle is repeated over a period that can range from a few minutes to hours. Film produced can be a few nanometers thin or thicker, e.g., 1 millimeter (mm).

The method of the invention also can be conducted using supercritical fluids. Examples of film deposition methods that use supercritical fluid that are currently known in the art include chemical fluid deposition; supercritical fluid transport-chemical deposition; supercritical fluid chemical deposition; and supercritical immersion deposition.

Chemical fluid deposition processes, for example, are well suited for producing high purity films and for covering complex surfaces and filling of high-aspect-ratio features. Chemical fluid deposition is described, for instance, in U.S. Pat. No. 5,789,027. The use of supercritical fluids to form films also is described in U.S. Pat. No. 6,541,278 B2. The disclosures of these two patents are incorporated herein by reference in their entirety.

In an embodiment of the invention, a heated patterned substrate is exposed to one or more organometallic compound precursors, in the presence of a solvent, such as a near critical or supercritical fluid, e.g., near critical or supercritical $CO_2$. In the case of $CO_2$, the solvent fluid is provided at a pressure above about 1000 psig and a temperature of at least about 30° C.

The precursor is decomposed to form a metal film on the substrate. The reaction also generates organic material from the precursor. The organic material is solubilized by the solvent fluid and easily removed away from the substrate. Metal oxide films also can be formed, for example by using an oxidizing gas.

In an example, the deposition process is conducted in a reaction chamber that houses one or more substrates. The substrates are heated to the desired temperature by heating the entire chamber, for instance, by means of a furnace. Vapor of the organometallic compound can be produced, for example, by applying a vacuum to the chamber. For low boiling compounds, the chamber can be hot enough to cause vaporization of the compound. As the vapor contacts the heated substrate surface, it decomposes and forms a metal or metal oxide film. As described above, an organometallic compound precursor can be used alone or in combination with one or more components, such as, for example, other organometallic precursors, inert carrier gases or reactive gases.

In a system that can be used in producing films by the method of the invention, raw materials can be directed to a gas-blending manifold to produce process gas that is supplied to a deposition reactor, where film growth is conducted. Raw materials include, but are not limited to, carrier gases, reactive gases, purge gases, precursor, etch/clean gases, and others. Precise control of the process gas composition is accomplished using mass-flow controllers, valves, pressure transducers, and other means, as known in the art. An exhaust manifold can convey gas exiting the deposition reactor, as well as a bypass stream, to a vacuum pump. An abatement system, downstream of the vacuum pump, can be used to remove any hazardous materials from the exhaust gas. The deposition system can be equipped with in-situ analysis system, including a residual gas analyzer, which permits measurement of the process gas composition. A control and data acquisition system can monitor the various process parameters (e.g., temperature, pressure, flow rate, etc.).

The organometallic compound precursors described above can be employed to produce films that include a single metal or a film that includes a single metal oxide. Mixed films also can be deposited, for instance mixed metal oxide films. Such films are produced, for example, by employing several organometallic precursors. Metal films also can be formed, for example, by using no carrier gas, vapor or other sources of oxygen.

Films formed by the methods described herein can be characterized by techniques known in the art, for instance, by X-ray diffraction, Auger spectroscopy, X-ray photoelectron emission spectroscopy, atomic force microscopy, scanning electron microscopy, and other techniques known in the art. Resistivity and thermal stability of the films also can be measured, by methods known in the art.

Atomic layer deposition and chemical vapor deposition of silicates and silicides can be useful for many next generation materials (e.g., hafnium silicates for dielectrics, tantalum silicon nitride for electrode or barrier). The versatility of the organometallic precursor compounds of this invention, which can be more reactive silicon precursors and deposit both mixed silicate/silicides and nanolaminate structures, would be highly beneficial.

Various modifications and variations of this invention will be obvious to a worker skilled in the art and it is to be understood that such modifications and variations are to be included within the purview of this application and the spirit and scope of the claims.

EXAMPLES

Synthesis of $Si(N(CH_3)_2)_3(NH_2)$

Under an inert atmosphere (nitrogen), 2 molar equivalents of $LiNH_2$ were added to 1 molar equivalent of $Si(N(CH_3)_2)_3Cl$ in tetrahydrofuran solvent. The reaction was stirred at a temperature of 25° C. for a period of 48 hours. Monitoring of the reaction was done by gas chromatography/mass spectrometry in which both $Si(N(CH_3)_2)_3Cl$ and $Si(N(CH_3)_2)_3(NH_2)$ parent ions were observed. Once conversion was complete, the solvent was removed, and the product was isolated by distillation as a clear colorless liquid. $^1$H NMR (300 MHz, $C_6D_6$, δ): 2.52 (s, 18H), 0.25 (br t, 2H, 50 Hz). GC-MS (m/z, %): 176 (100), 132 (100), 116 (33).

Atomic Layer Deposition of $SiO_2$ Comparing $Si(N(CH_3)_2)_4$ and $Si(N(CH_3)_2)_3(NH_2)$ Precursors The utility of $Si(N(CH_3)_2)_3(NH_2)$ was evaluated by comparing performance to the known precursor $Si(N(CH_3)_2)_4$. An experiment using atomic layer deposition of $SiO_2$ was undertaken, utilizing growth rates as the basis for comparison. The conditions of the experiment were as follows: silicon substrates, wafer temperature at 330° C., pressure of 5 torr, precursor flow about 0.7 standard cubic centimeters per minute (based on thermogravimetric analysis vaporization rates), 4 step cycles, precursor/purge/co-reactant/purge, 10/20/10/20 seconds. Argon was utilized as the carrier gas. The co-reactant was an $Ar/O_2$ plasma (10 Watts load). Thickness was measured by variable angle spectroscopic ellipsometry. Minimal thickness contributions related to growth of $SiO_2$ due to $O_2$ plasma alone were taken into account. The results showed that $Si(N(CH_3)_2)_3(NH_2)$ produced an $SiO_2$ film at over twice the growth rate of $Si(N(CH_3)_2)_4$ (0.054 nanometers/cycle vs. 0.023 nanometers/cycle).

The invention claimed is:

1. An organometallic precursor compound represented by the formula: $M(NR'_1R'_2)_q$ wherein M is a metal or metalloid, $R'_1$ is the same or different and is a hydrocarbon group or a heteroatom-containing group, $R'_2$ is the same or different and is a hydrocarbon group or a heteroatom-containing group; when q is a value of 2 or greater, $R'_1$ or $R'_2$ of one $(NR'_1R'_2)$ group can be combined with $R'_1$ or $R'_2$ of another $(NR'_1R'_2)$ group to form a substituted or unsubstituted, saturated or unsaturated cyclic group; q+2 is a value equal to the oxidation state of M, and: represents 2 electrons; wherein the organometallic compound is a liquid at 20° C., wherein M is Si, Ti, Zr, Hf, V, Nb, Ta, Cr, Mo, W, Al, Ga, Ge, a Lanthanide series element or an Actinide series element; and each of $R'_1$ and $R'_2$ is the same or different and is independently hydrogen, alkyl; a substituted or unsubstituted, saturated or unsaturated, hydrocarbon, aromatic hydrocarbon, cycloaliphatic hydrocarbon, aromatic heterocycle, cycloaliphatic heterocycle, alkyl halide, silylated hydrocarbon, ether, polyether, thioether, ester, lactone, amide, amine, polyamine, nitrile; or mixtures thereof.

2. An organometallic precursor compound represented by the formula : $M(NR'_1R'_2)_q$ wherein M is a metal or metalloid, $R'_1$ is the same or different and is a hydrocarbon group or a heteroatom-containing group, $R'_2$ is the same or different and is a hydrocarbon group or a heteroatom-containing group; when q is a value of 2 or greater, $R'_1$ or $R'_2$ of one $(NR'_1R'_2)$ group can be combined with $R'_1$ or $R'_2$ of another $(NR'_1R'_2)$ group to form a substituted or unsubstituted, saturated or unsaturated cyclic group; q+2 is a value equal to the oxidation state of M, and : represents 2 electrons; wherein the organometallic compound is a liquid at 20° C., and further wherein the organometallic precursor compound is selected from N,N'-di-tert-butylethene-1,2-diaminosilylene, N,N'-di-tert-butylethylene-1,2-diaminosilylene, N,N'-diisopropylethene-1,2-diaminosilylene, bis(di-tert-butylamino)silylene, and bis(di-tert-amylamino)silylene.

* * * * *